US009680173B2

(12) United States Patent
Takaki et al.

(10) Patent No.: US 9,680,173 B2
(45) Date of Patent: Jun. 13, 2017

(54) ENERGY SAVING METHOD IN COMBINED SYSTEM OF BIOETHANOL PRODUCING DEVICE AND SOLID OXIDE FUEL CELL

(71) Applicant: Hitachi Zosen Corporation, Osaka-shi (JP)

(72) Inventors: Yoshinobu Takaki, Osaka (JP); Masato Kawami, Osaka (JP); Yoshihiro Asari, Osaka (JP); Yoshinori Sakai, Osaka (JP); Daisuke Hashimoto, Osaka (JP)

(73) Assignee: Hitachi Zosen Corporation, Osaka-shi (JP)

( * ) Notice: Subject to any disclaimer, the term of this patent is extended or adjusted under 35 U.S.C. 154(b) by 0 days.

(21) Appl. No.: 14/899,257

(22) PCT Filed: Jun. 13, 2014

(86) PCT No.: PCT/JP2014/065666
§ 371 (c)(1),
(2) Date: Dec. 17, 2015

(87) PCT Pub. No.: WO2014/203806
PCT Pub. Date: Dec. 24, 2014

(65) Prior Publication Data
US 2016/0149243 A1    May 26, 2016

(30) Foreign Application Priority Data

Jun. 17, 2013   (JP) .................. 2013-126296

(51) Int. Cl.
*H01M 8/04828*  (2016.01)
*C12M 1/00*  (2006.01)
(Continued)

(52) U.S. Cl.
CPC ......... *H01M 8/04828* (2013.01); *C01B 3/323* (2013.01); *C12M 21/12* (2013.01);
(Continued)

(58) Field of Classification Search
CPC ........ Y02P 20/128; Y02P 20/52; Y02P 30/30; Y02P 70/56; Y02P 20/125; Y02P 20/129;
(Continued)

(56) References Cited

U.S. PATENT DOCUMENTS 5,736,026 A    4/1998 Patel et al.
2005/0181247 A1    8/2005 Foger et al.
(Continued)

FOREIGN PATENT DOCUMENTS

EP    1768207 A1    3/2007
JP    2005-535068 A    11/2005
(Continued)

OTHER PUBLICATIONS

Athanasios N. Fatsikostas et al., "Production of hydrogen for fuel cells by reformation of biomass-derived ethanol," Catalysis Today 75, 2002, pp. 145-155.
(Continued)

*Primary Examiner* — Lucas J. O'Donnell
(74) *Attorney, Agent, or Firm* — Locke Lord LLP

(57) ABSTRACT

The present invention is to provide, in a combined system of a bioethanol producing device and an SOFC, a method that is capable of further enhancing the electric power generation efficiency of the SOFC, and is also capable of achieving further reduction of the energy required for distillation of the fermented liquid. A part of an anode off-gas is refluxed to the water-containing ethanol vapor line from the mash column to the reforming device at a reflux ratio (((flow rate of reflux gas)/(flow rate of (anode off-gas)−(reflux gas))) of from 1 to 2. The ethanol concentration of the water-containing ethanol vapor is controlled by refluxing, to a range of from 25 to 35% by weight with water contained in the anode off-gas of the solid oxide fuel cell.

6 Claims, 3 Drawing Sheets

(51) Int. Cl.
  *C12P 7/06* (2006.01)
  *C01B 3/32* (2006.01)
  *H01M 8/04014* (2016.01)
  *H01M 8/0612* (2016.01)
  *H01M 8/1246* (2016.01)
  *H01M 8/04089* (2016.01)
  *H01M 8/124* (2016.01)

(52) U.S. Cl.
  CPC ............... *C12M 43/08* (2013.01); *C12P 7/06* (2013.01); *H01M 8/04022* (2013.01); *H01M 8/04097* (2013.01); *H01M 8/04835* (2013.01); *H01M 8/0618* (2013.01); *H01M 8/1246* (2013.01); *C01B 2203/0233* (2013.01); *C01B 2203/066* (2013.01); *C01B 2203/0811* (2013.01); *C01B 2203/1229* (2013.01); *C01B 2203/1288* (2013.01); *C01B 2203/169* (2013.01); *H01M 2008/1293* (2013.01); *H01M 2300/0071* (2013.01); *Y02E 50/17* (2013.01); *Y02P 70/56* (2015.11)

(58) Field of Classification Search
  CPC ...... Y02P 20/142; Y02P 20/145; Y02P 20/13; Y02P 30/20; Y02P 20/124; H01M 8/0612; H01M 8/0631; H01M 8/0643; H01M 8/061
  See application file for complete search history.

(56) References Cited

U.S. PATENT DOCUMENTS

| | | | |
|---|---|---|---|
| 2007/0092435 | A1 | 4/2007 | Essaki et al. |
| 2008/0070077 | A1 | 3/2008 | Gottmann |

FOREIGN PATENT DOCUMENTS

| | | |
|---|---|---|
| JP | 2007-020407 A | 2/2007 |
| JP | 2007-076954 A | 3/2007 |
| JP | 2007-128680 A | 5/2007 |
| JP | 2007-311072 A | 11/2007 |
| JP | 2011-187328 A | 9/2011 |
| JP | 2012-111725 A | 6/2012 |
| WO | 2007/137068 A1 | 11/2007 |

OTHER PUBLICATIONS

International Search Report mailed Sep. 9, 2014, issued for PCT/JP2014/065666.
Supplementary European Search Report dated Nov. 30, 2016, issued for the European patent application No. 14813205.3.
Office Action dated Aug. 2, 2016, issued for Japanese patent application No. 2015-522869.

Relationship between Overhead Vapor Concentration and Consumption Energy in Mash Column

ENERGY SAVING METHOD IN COMBINED SYSTEM OF BIOETHANOL PRODUCING DEVICE AND SOLID OXIDE FUEL CELL

TECHNICAL FIELD

The present invention relates to an energy saving method in a combined system of a bioethanol producing device and a solid oxide fuel cell (which may be hereinafter referred to as "SOFC").

BACKGROUND ART

Bioethanol has a problem of consuming a large amount of energy for ethanol enrichment and distillation-purification since an automobile fuel requires high concentration ethanol of 99.5% by weight or more.

An SOFC system is equipped with a reforming device that vaporizes and reforms an ethanol aqueous solution of from 25 to 35% by weight to generate hydrogen gas, and an SOFC that generates electric power with the hydrogen gas, and thus does not require a distillation-purification column.

Under the circumstances, some proposals have been made for a system that intends to reduce the consumption energy cost and the equipment cost by combining a bioethanol producing device and an SOFC.

For example, PTL 1 proposes a combined system equipped with a means for withdrawing water-containing ethanol vapor having a concentration of from 30 to 70% by weight from an overhead of a distillation column of a bioethanol producing device, and a reforming means for producing a reformed gas from the overhead vapor, and also equipped with a SOFC operated with the reformed gas as a fuel.

PTL 2 describes a fuel cell system having a reforming device forming a reformed gas containing hydrogen from a hydrocarbon raw material supplied through reformation reaction including steam reformation reaction, a fuel cell performing electric power generation by supplying the reformed gas to an anode, and an anode off-gas introducing means for introducing at least a part of an anode off-gas containing water formed in association with the electric power generation to an inlet port of the reforming device through an ejector.

PTL 3 describes a fuel cell electric power generation system performing electric power generation in such a manner that an ethanol fuel having a concentration of from 15.4 to 46% by weight obtained from an ethanol fermented liquid is vaporized to form a mixed gas of steam and ethanol, which is reformed by being supplied to a reformation reaction zone to generate a reformed gas containing hydrogen, and the reformed gas is supplied to an SOFC.

NPL 1 reports a study on a method for providing a hydrogen rich gas suitable for supplying to a fuel cell, through steam reformation of bioethanol, in which FIG. 1 shows an electric power generation system having a step of providing a water-containing ethanol vapor of from 45 to 55% by weight through distillation of an ethanol fermented liquid, a step of reforming the water-containing ethanol vapor to form a reformed gas containing hydrogen, and a step of performing electric power generation with a fuel cell using the reformed gas as a fuel, and also shows that the heat of the off-gas discharged from the fuel cell is sent to and utilized in the distillation step and the reformation step.

CITATION LIST

Patent Literatures

PTL 1: JP-A-2007-20407
PTL 2: JP-A-2007-128680
PTL 3: JP-A-2011-187328

Non Patent Literature

NPL 1: Catalysis Today, 75 (2002), pp. 145-155

SUMMARY OF THE INVENTION

Problem to be Solved by the Invention

The techniques shown above as the background art achieve reduction of the consumption energy in the production of bioethanol to a certain extent but are still not satisfactory.

Under the circumstances, an object of the invention is to provide, in a combined system of a bioethanol producing device and an SOFC, a method that is capable of further enhancing the electric power generation efficiency of the SOFC, and is also capable of achieving further reduction of the energy required for distillation of the fermented liquid.

Means for Solving the Problem

The invention according to claim 1 relates to an energy saving method in a combined system of a bioethanol producing device and a solid oxide fuel cell, in a combined system containing a mash column that distills a fermented liquid formed in a fermenting vessel of a bioethanol producing device to distill off a water-containing ethanol vapor from an overhead thereof, a reforming device that forms a reformed gas from the water-containing ethanol vapor, and a solid oxide fuel cell that is operated with the reformed gas as a fuel, the method including refluxing a part of an anode off-gas of the solid oxide fuel cell to a water-containing ethanol vapor line from the mash column to the reforming device at a reflux ratio ((flow rate of reflux gas)/(flow rate of (anode off-gas)−(reflux gas))) of from 1 to 2, so as to control an ethanol concentration of the water-containing ethanol vapor to a range of from 25 to 35% by weight with water contained in the anode off-gas of the solid oxide fuel cell.

The anode off-gas contains water generated through the electric power generation of the SOFC, and thus the ethanol concentration of the water-containing ethanol vapor, which is to be supplied to the reforming device, can be controlled to a range of from 25 to 35% by weight with water contained in the anode off-gas, by refluxing a part of the anode off-gas to the water-containing ethanol vapor line from the mash column to the reforming device at the prescribed reflux ratio.

The reflux ratio is preferably in a range of from 1.2 to 1.8. When the reflux ratio is less than 1, the electric power generation efficiency of the SOFC may not be enhanced. When the reflux ratio is exceeding 1, the electric power generation efficiency of the SOFC and the total thermal efficiency may be increased, but when the reflux ratio exceeds 2, the efficiencies may be saturated but may not be further increased. Furthermore, the increase of the reflux ratio requires the increase of the loads of the blower and the ejector, and also in this point of view, the upper limit of the reflux ratio is 2.

The invention according to claim 2 relates to the energy saving method in a combined system of a bioethanol producing device and a solid oxide fuel cell according to claim 1, wherein the ethanol concentration of the water-containing ethanol vapor distilled off from the mash column is controlled to a range of from 35 to 60% by weight.

The invention according to claim 3 relates to the energy saving method in a combined system of a bioethanol producing device and a solid oxide fuel cell according to claim 1, wherein the ethanol concentration of the water-containing ethanol vapor distilled off from the mash column is controlled to a range of from 55 to 60% by weight.

The invention according to claim 4 relates to the energy saving method in a combined system of a bioethanol producing device and a solid oxide fuel cell according to any one of claims 1 to 3, wherein the balance of the anode off-gas of the solid oxide fuel cell and a cathode off-gas thereof are supplied to a catalytic combustor for the reforming device and a catalytic combustor for a reboiler of the mash column, so as to combust a combustible component in the anode off-gas with oxygen in the cathode off-gas, and heat generated in the catalytic combustor for the reforming device is used for heating the reforming device, whereas heat generated in the catalytic combustor for the reboiler is used for heating a bottom liquid of the mash column.

The anode off-gas contains combustible components, such as $H_2$ (3 to 10% by volume) and CO (0 to 10% by volume), and the cathode off-gas contains from 5 to 10% by volume of oxygen. Accordingly, the combustible components are combusted with the oxygen in catalytic combustors, and heat generated therein is effectively used for heating the reforming device and the bottom liquid of the mash column. The catalytic combustor for the reforming device and the catalytic combustor for the reboiler each may be a known one.

Advantageous Effects of Invention

1. For vaporizing and reforming ethanol in the reforming device through sufficient and durable exhibition of the capability of the reformation catalyst to generate hydrogen gas, it is necessary to control the ethanol concentration of the water-containing ethanol vapor to a range of from 25 to 35% by weight.

In the invention according to claim 1, apart of the anode off-gas from the SOFC is refluxed to the water-containing ethanol vapor line from the mash column to the reforming device at a reflux ratio ((flow rate of reflux gas)/(flow rate of (anode off-gas)−(reflux gas))) of from 1 to 2, so as to control the ethanol concentration of the water-containing ethanol vapor, which is to be supplied to the reforming device, to a range of from 25 to 35% by weight with water contained in the anode off-gas.

2. In an SOFC cell stack, the utilization rate of the combustible component (such as $H_2$ and CO) in the anode supply gas is generally approximately 70%. This is because the cell may be damaged if the concentration of the combustible component in the anode supply gas is too small.

In the invention according to claim 1, apart of the anode off-gas is refluxed to the water-containing ethanol vapor line from the mash column to the reforming device at the prescribed reflux ratio as described above, by which the concentration of the combustible component in the anode supply gas can be increased, so as to enhance the utilization rate of the fuel to approximately 90%, and thus the electric power generation efficiency can be enhanced.

3. In the reforming device, it is necessary to control the ethanol concentration of the water-containing ethanol vapor to a range of from 25 to 35% by weight, but in the case where a water-containing ethanol vapor that has an ethanol concentration in a range of from 25 to 35% by weight is to be distilled off from the overhead of the mash column, a large amount of energy may be consumed. In the invention according to claim 1, the ethanol concentration of the water-containing ethanol vapor can be controlled to a range of from 25 to 35% by weight by refluxing a part of the anode off-gas to the water-containing ethanol vapor line from the mash column to the reforming device at the prescribed reflux ratio as described above, by which the ethanol concentration of the water-containing ethanol vapor thus distilled off from the mash column may be from 35 to 60% by weight, and further from 55 to 60% by weight, and thereby the consumption energy of the reboiler of the mash column can be suppressed to the requisite minimum level.

4. In the invention according to claim 4, the balance of the anode off-gas of the SOFC and the cathode off-gas thereof are supplied to the catalytic combustor for the reforming device and the catalytic combustor for the reboiler of the mash column, so as to combust the combustible component (such as $H_2$ and CO) in the anode off-gas with oxygen in the cathode off-gas, and thus heat can be generated in the catalytic combustor for the reforming device and the catalytic combustor for the reboiler, and can be effectively utilized for heating the reforming device and the bottom liquid of the mash column.

EMBODIMENTS OF INVENTION

Figure 1:
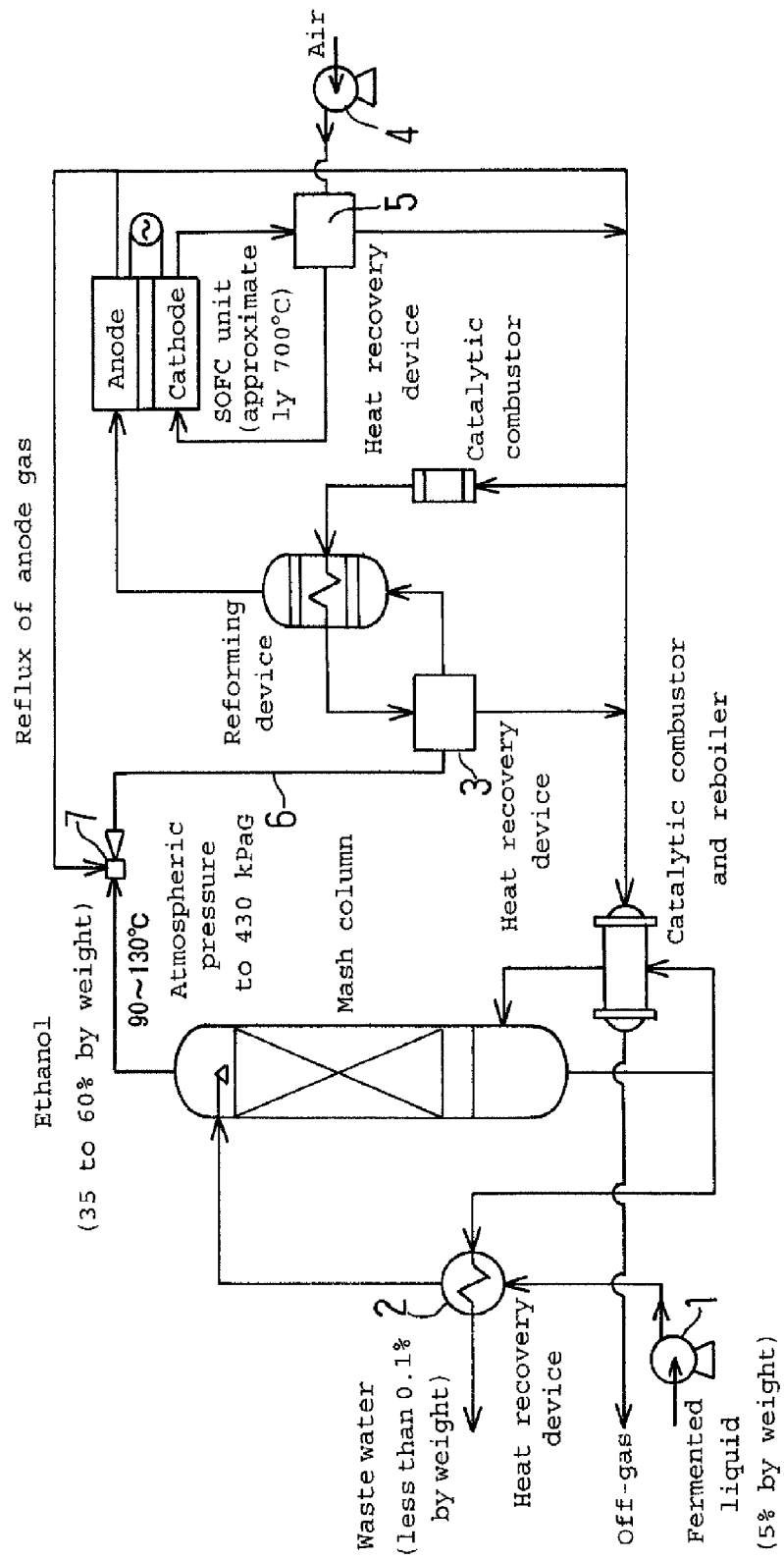
FIG. 1 is a flow diagram showing an embodiment of the invention.
Figure 2:
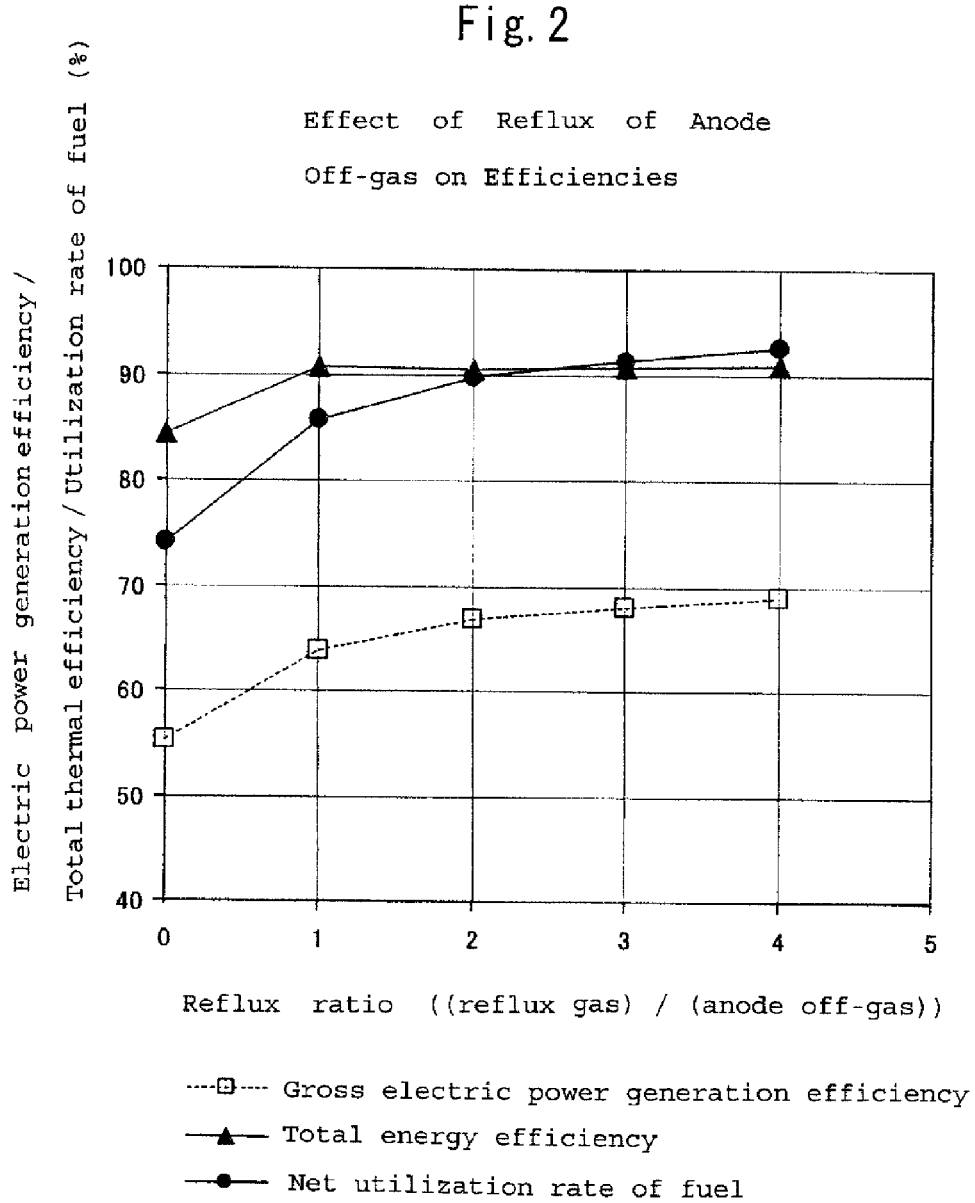
FIG. 2 is a graph showing the effect of refluxing the anode off-gas on the efficiencies.

The invention will be described below with reference to embodiments shown in the drawings.

In FIG. 1, the combined system of a bioethanol producing device and an SOFC according to the invention is constituted by the combination of a mash column that distills a fermented liquid formed in a fermenting vessel of a bioethanol producing device for distilling off a water-containing ethanol vapor from an overhead thereof, a reforming device that forms a reformed gas from the water-containing ethanol vapor, and a solid oxide fuel cell that is operated with the reformed gas as a fuel.

In the system, a fermented liquid having an ethanol concentration of 5% by weight is supplied to the overhead of the mash column with a pump (1) through a heat recovery device (2). The mash column, for example, has a number of distillation plates of 40, and distills the fermented liquid at a temperature in a range of from 100 to 154° C. The bottom liquid is withdrawn from the bottom of the mash column, and a part of the bottom liquid is heated with a catalytic combustor and a reboiler and then returned to the bottom of the mash column, whereas the balance of the bottom liquid is discharged as waste water having an ethanol concentration of less than 0.1% by weight through the heat recovery device (2).

On the other hand, a water-containing ethanol vapor having an ethanol concentration of from 35 to 60% by weight is distilled off from the overhead of the mash column at a temperature of from 90 to 130° C. and a pressure of from the atmospheric pressure to 430 kPaG. The water-containing ethanol vapor is sent to the reforming device through a heat recovery device (3), and in the reforming device, ethanol is vaporized and reformed to generate a reformed gas containing hydrogen. The reformed gas is sent to the anode of the SOFC unit operated at approximately 700° C., and utilized for electric power generation. Air is supplied to the cathode of the SOFC unit with a blower (4) through a heat recovery device (5), and oxygen in the air is used for electric power generation.

A part of the anode off-gas is refluxed to an ejector (7) provided in the course of the water-containing ethanol vapor line (6) from the overhead of the mash column to the reforming device at a reflux ratio ((flow rate of reflux gas)/(flow rate of (anode off-gas)−(reflux gas))) of approximately 1.5. The ethanol concentration of the water-containing ethanol vapor is controlled by refluxing, to a range of from 25 to 35% by weight with water contained in the anode off-gas of the SOFC.

A part of the anode off-gas is thus refluxed to the water-containing ethanol vapor line from the mash column to the reforming device at the prescribed reflux ratio as described above, by which the concentration of the combustible component (such as $H_2$ and CO) in the anode supply gas can be increased, so as to enhance the utilization rate of the fuel to approximately 90%, and thus the electric power generation efficiency can be enhanced.

Furthermore, apart of the anode off-gas is thus refluxed to the water-containing ethanol vapor line from the mash column to the reforming device at the prescribed reflux ratio as described above, by which the ethanol concentration of the water-containing ethanol vapor, which is distilled off from the mash column at a temperature of from 90 to 130° C. and a pressure of from the atmospheric pressure to 430 kPaG, can be controlled to a range of from 25 to 35% by weight (assuming that the reflux ratio is from 1 to 2). Thus, the consumption energy of the reboiler of the mash column can be suppressed to the requisite minimum level.

The balance of the anode off-gas of the SOFC and the cathode off-gas thereof are combined, and at least a part of the combined gas is diverted to pass through the catalytic combustor for the reforming device, the reforming device and the heat recovery device (3), and then combined with the balance of the combined gas that is not diverted. In the catalytic combustor for the reforming device, the combustible component (such as $H_2$ and CO) derived from the anode off-gas is combusted with oxygen derived from the cathode off-gas, and the heat thus generated is used for heating the reforming device. The combined gas is also sent to the catalytic combustor for the reboiler of the mash column, in which also the combustible component (such as $H_2$ and CO) derived from the anode off-gas is combusted with oxygen derived from the cathode off-gas, and the heat thus generated is used for heating the bottom liquid of the mash column.

Figure 3:
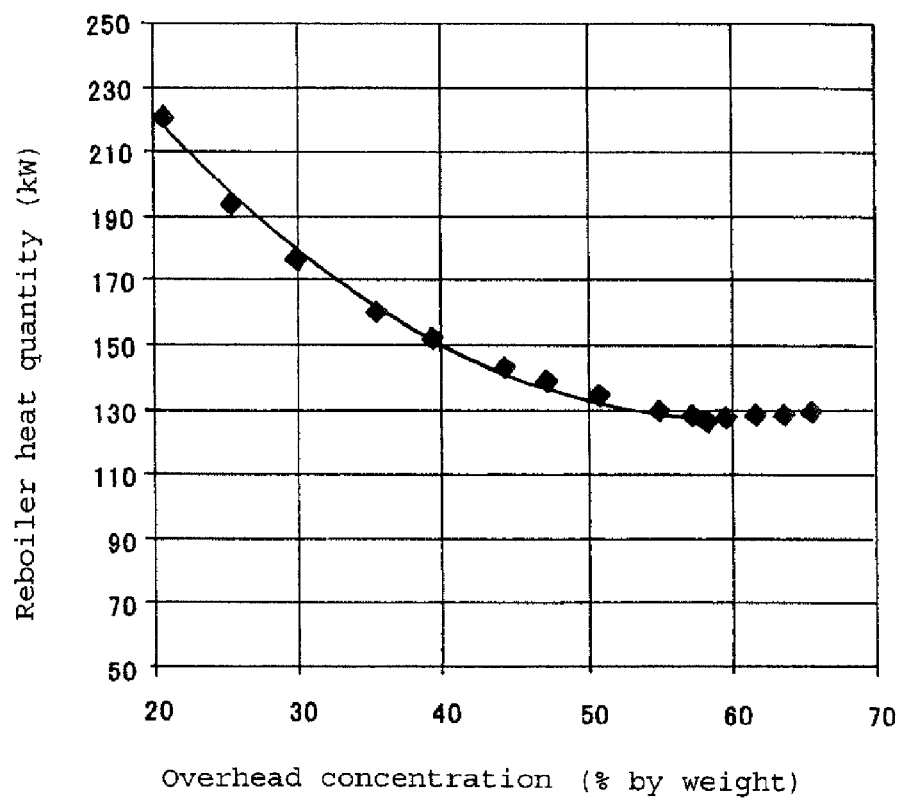
FIG. 3 is a graph showing the relationship between the overhead vapor concentration and the consumption energy in the mash column.

FIG. 3 shows the relationship between the overhead vapor concentration of the mash column and the consumption energy. The graph in the figure shows the result obtained by calculating the change of the reboiler heat quantity that is required for dehydrating and enriching a fermented liquid having an ethanol concentration of 5% by weight at an overhead pressure of 50 kPaG, depending on the change of the overhead vapor concentration. In the reforming device, for vaporizing and reforming ethanol through sufficient and durable exhibition of the capability of the reformation catalyst to generate hydrogen gas, it is necessary to control the ethanol concentration of the water-containing ethanol vapor to a range of from 25 to 35% by weight, and in the mash column, the consumption energy is minimized under the condition that water-containing ethanol is enriched to an ethanol concentration in a range of from 35 to 60% by weight. The consumption energy is increased under the condition that water-containing ethanol is enriched to a range exceeding 60% by weight. The reboiler heat quantity is calculated by using a process simulator (ASPEN). It is assumed that a fermented liquid having an ethanol concentration of 5% by weight is distilled at approximately 90° C. with a number of distillation plates of the distillation column of 40. In the region where the overhead vapor concentration of the distillation column is in a low concentration range, an operation referred to as simple distillation is performed, and with the increase of the concentration, the latent heat of vaporization of water is decreased to reduce the reboiler heat quantity. When the concentration is the certain value (which is approximately 55% by weight found by trial calculation), further enrichment cannot be performed by simple distillation, and a refluxing operation is required, which increases the reboiler heat quantity. In a range of enrichment of the concentration higher than the value, the consumption energy is simply increased.

INDUSTRIAL APPLICABILITY

In a combined system of a bioethanol producing device and an SOFC, the invention can be effectively applied thereto for further enhancing the electric power generation efficiency of the SOFC and for further reducing the energy required for distillation of a fermented liquid.

The invention claimed is:
1. An energy saving method in a combined system of a bioethanol producing device and a solid oxide fuel cell,
in a combined system containing a mash column that distills a fermented liquid formed in a fermenting vessel of a bioethanol producing device to distill off a water-containing ethanol vapor from an overhead thereof, a reforming device that forms a reformed gas from the water-containing ethanol vapor, and a solid oxide fuel cell that is operated with the reformed gas as a fuel,
the method comprising refluxing a part of an anode off-gas of the solid oxide fuel cell to a water-containing ethanol vapor line from the mash column to the reforming device at a reflux ratio ((flow rate of reflux gas)/(flow rate of (anode off-gas)−(reflux gas))) of from 1 to 2, so as to control an ethanol concentration of the water-containing ethanol vapor to a range of from 25 to 35% by weight with water contained in the anode off-gas of the solid oxide fuel cell.

2. The energy saving method in a combined system of a bioethanol producing device and a solid oxide fuel cell according to claim 1, wherein the ethanol concentration of the water-containing ethanol vapor distilled off from the mash column is controlled to a range of from 35 to 60% by weight.

3. The energy saving method in a combined system of a bioethanol producing device and a solid oxide fuel cell according to claim 1, wherein the ethanol concentration of the water-containing ethanol vapor distilled off from the mash column is controlled to a range of from 55 to 60% by weight.

4. The energy saving method in a combined system of a bioethanol producing device and a solid oxide fuel cell according to claim 1, wherein the balance of the anode off-gas of the solid oxide fuel cell and a cathode off-gas thereof are supplied to a catalytic combustor for the reforming device and a catalytic combustor for a reboiler of the mash column, so as to combust a combustible component in the anode off-gas with oxygen in the cathode off-gas, and heat generated in the catalytic combustor for the reforming device is used for heating the reforming device, whereas heat generated in the catalytic combustor for the reboiler is used for heating a bottom liquid of the mash column.

5. The energy saving method in a combined system of a bioethanol producing device and a solid oxide fuel cell according to claim 2, wherein the balance of the anode off-gas of the solid oxide fuel cell and a cathode off-gas thereof are supplied to a catalytic combustor for the reforming device and a catalytic combustor for a reboiler of the mash column, so as to combust a combustible component in the anode off-gas with oxygen in the cathode off-gas, and heat generated in the catalytic combustor for the reforming device is used for heating the reforming device, whereas heat generated in the catalytic combustor for the reboiler is used for heating a bottom liquid of the mash column.

6. The energy saving method in a combined system of a bioethanol producing device and a solid oxide fuel cell according to claim 3, wherein the balance of the anode off-gas of the solid oxide fuel cell and a cathode off-gas thereof are supplied to a catalytic combustor for the reforming device and a catalytic combustor for a reboiler of the mash column, so as to combust a combustible component in the anode off-gas with oxygen in the cathode off-gas, and heat generated in the catalytic combustor for the reforming device is used for heating the reforming device, whereas heat generated in the catalytic combustor for the reboiler is used for heating a bottom liquid of the mash column.

* * * * *